United States Patent
Kikuchi (10) Patent No.: US 8,503,611 B2
(45) Date of Patent: Aug. 6, 2013

(54) X-RAY TOPOGRAPHY APPARATUS

(75) Inventor: Tetsuo Kikuchi, Tachikawa (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 306 days.

(21) Appl. No.: 12/983,359

(22) Filed: Jan. 3, 2011

(65) Prior Publication Data

US 2011/0164729 A1 Jul. 7, 2011

(30) Foreign Application Priority Data

Jan. 6, 2010 (JP) .................. 2010-000932

(51) Int. Cl.
*G01N 23/207* (2006.01)
(52) U.S. Cl.
USPC .................................................. 378/74
(58) Field of Classification Search
USPC .......................................... 378/70, 71, 73, 74
See application file for complete search history.

(56) References Cited

U.S. PATENT DOCUMENTS

| | | |
|---|---|---|
| 2005/0084065 A1 | 4/2005 | Taguchi |
| 2009/0225945 A1 * | 9/2009 | Smither ..................... 378/71 |

FOREIGN PATENT DOCUMENTS

| | | |
|---|---|---|
| JP | 03-167458 A | 7/1991 |
| JP | 05-264475 A | 10/1993 |
| JP | 5-289190 A | 11/1993 |
| JP | 10-313383 A | 11/1998 |
| JP | 11-014564 A | 1/1999 |
| JP | 2000-314708 A | 11/2000 |
| JP | 2005-121511 A | 5/2005 |
| JP | 2006-071321 A | 3/2006 |
| WO | WO 2006/039919 A1 | 4/2006 |
| WO | WO 2006039919 * | 4/2006 |

OTHER PUBLICATIONS

Office Action (Notification of Reasons for Rejection) dated Feb. 1, 2012, issued in the corresponding Japanese Patent Application No. 2010-000932, and an English Translation thereof. (9 pages).

* cited by examiner

*Primary Examiner* — Jurie Yun
(74) *Attorney, Agent, or Firm* — Buchanan Ingersoll & Rooney PC (57) ABSTRACT

An x-ray topography apparatus in which x-rays diffracted from a sample which is scanned with a linear x-ray are detected by an x-ray detector to obtain a planar diffraction image. In this x-ray topography apparatus, the x-ray detector is an imaging plate shaped as a cylinder and provided with a surface area that is larger than the sample, and the imaging plate is made to undergo α-rotation about the center axis of the cylindrical shape in coordination with scanning movement of the linear x-rays. The center axis of the cylindrical shape extends in a direction at a right angle with respect to the direction of the scanning movement of the linear x-rays.

12 Claims, 9 Drawing Sheets

X-RAY TOPOGRAPHY APPARATUS

BACKGROUND OF THE INVENTION

1. Field of the Invention

The present invention relates to an x-ray topography apparatus, which is an apparatus for displaying an x-ray diffraction image representing a two-dimensional image of a crystalline structure in the interior of an object.

2. Description of the Related Art

The two-dimensional, namely planar, x-ray diffraction image obtained using an x-ray topography apparatus is called an x-ray topograph. The morphological features revealed in the x-ray topograph typically represent structural features of the object. For example, lattice defects or distortion in single crystals appear as changes in x-ray intensity in the x-ray topograph. For this reason, x-ray topography apparatuses currently enjoy widespread use as apparatuses for carrying out "evaluation on integrity of crystals" in relation to single crystal materials.

For example, in the case of production facilities for Si (silicon) crystal, which is a single crystal material, the wafer diameter has progressively increased over time, and the larger diameters have resulted in an associated increase in size of the measuring instruments, i.e., x-ray topography apparatuses. Specifically, whereas Si crystals have a diameter of about 4 inches (101.6 mm) at the beginning, larger sizes of up to about 300 mm have recently been achieved. Even larger Si crystal sizes, e.g., up to about 450 mm, are anticipated in the near future.

Known x-ray topography apparatus include those disclosed, for example, in Japanese Laid-Open Patent Applications H11-014564 and 2000-314708. Japanese Laid-Open Patent Application H11-014564 discloses an x-ray topography apparatus adapted to produce an x-ray topograph on a flat x-ray fluorescent plate or a flat storage phosphor. Japanese Laid-Open Patent Application 2000-314708 discloses an x-ray topography apparatus adapted to produce an x-ray topograph on a flat x-ray film or flat CCD (charge coupled device) sensor.

There are a number of different types of x-ray topography apparatus. For example, known x-ray topography techniques include the Berg-Barrett method, which is a reflectional and single crystal technique; the Lang method, which is a transmissive and single crystal technique; and double crystal methods that use a crystal other than the sample as a monochromator or collimator. As regards the Lang method, a construction like that depicted in FIG. 9A, for example, is known.

Figure 9A:
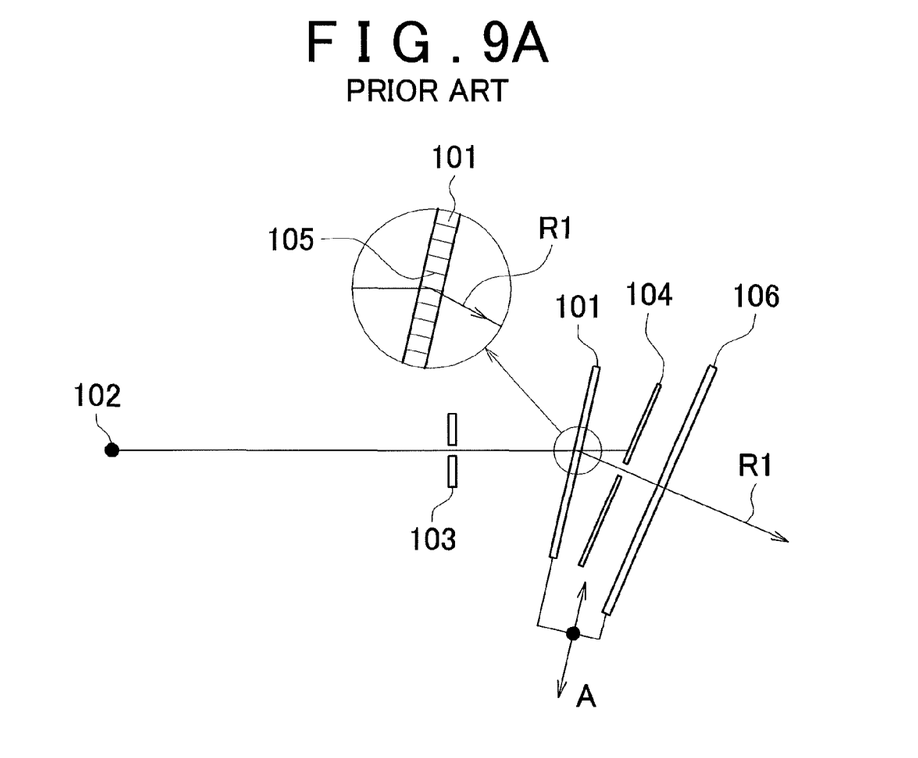
FIG. 9A is a drawing depicting a prior art x-ray topography apparatus, and shows a device in which a diffracted x-ray is perpendicularly incident to an x-ray detection film.

The x-ray topography apparatus depicted in FIG. 9A, which is based on the Lang method, has an x-ray source 102 that emits x-rays to be directed onto a sample crystal 101, and also has an entry slit 103 positioned on the incident side of the sample crystal 101. X-rays are regulated by the entry slit 103 and enter the sample crystal 101. The light receiving side of the sample crystal 101 is provided with a diffraction slit 104 and a flat x-ray detection film 106. Previously, when the diameter of the sample 101 was smaller, the x-ray detection film 106 was a nuclear plate composed of a glass substrate coated with a thick coating (50-100 μm) of an emulsion, for example.

The entry slit 103 and the diffraction slit 104 are immovably fixed. As indicated by the arrow A, the sample crystal 101 and the x-ray detection film 106, in unison with one another, undergo scanning movement parallel to the sample face, i.e., the measured face, of the sample 101. During this scanning movement, as depicted by the fragmentary enlarged view in FIG. 9A, the x-ray detection film 106 is exposed by a diffracted x-ray R1 which has been diffracted at the lattice plane 105 of the sample crystal 101.

In this previous x-ray topography apparatus, the positional relationships of the sample crystal 101, the diffraction slit 104, and the x-ray detection film 106 are set such that an x-ray diffracted by the sample crystal 101 impinges in the vertical direction onto the x-ray detection film 106. The reason for doing so is that if an x-ray impinges obliquely on the thick emulsion coating of the x-ray detection film 106, the diffraction image may become blurred, and resolution may be reduced; therefore, the aim is to prevent such a decrease in resolution.

In order to make a diffracted x-ray impinge vertically on the x-ray detection film 106, it is thus necessary to position the diffraction slit 104 obliquely with respect to the sample crystal 101. On the other hand, the slit piece of the immobilized diffraction slit 104 must have a width that matches the size of the x-ray detection film, in order to prevent fogging by scattered x-rays. By doing this, during scanning of the sample crystal 101 and the x-ray detection film 106, there is risk of the sample crystal 101 colliding with the diffraction slit 104; however, when the diameter of the sample crystal 101 is small, the gap between the sample crystal 101 and the x-ray detection film 106 does not need to be very big, so this has not been a problem.

However, with a larger diameter of the sample crystal 101, the sample crystal 101 and the x-ray detection film 106 must be separated by a large gap in order to prevent collision of the sample crystal 101 and the diffraction slit 104. In such instances, a problem can be presented in regard to an excessively large gap being created at the end where a larger gap exists between the sample crystal 101 and the x-ray detection film 106, resulting in degraded x-ray optical resolution in this part.

Figure 9B:
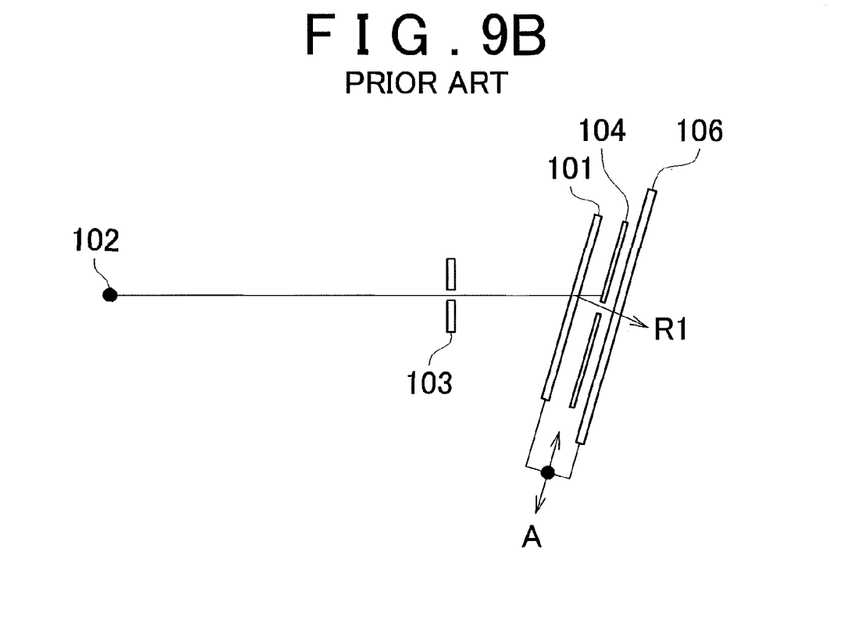
FIG. 9B is a drawing depicting a prior art x-ray topography apparatus, and shows a device in which a sample and a diffraction slit are disposed in parallel.

To address this problem when a large-diameter sample crystal 101 is used, there have been adopted configurations such as that depicted in FIG. 9B, in which both the diffraction slit 104 and the x-ray detection film 106 are oriented parallel to the sample crystal 101. Such systems are widely employed in apparatuses for sample crystals 101 with diameters of 100 mm and above.

In this apparatus, while collision of the sample crystal 101 with the diffraction slit 104 may be avoided, the diffracted x-ray R1 obliquely impinges on the x-ray detection film 106, and diffraction image blur becomes a concern. However, by using an x-ray detection film 106 with a thinner emulsion coating, improved resolution is possible due to the smaller gap between the sample crystal 101 and the x-ray detection film 106, which more than compensates for degradation of resolution resulting from oblique incidence.

For example, in the case of MoKα rays impinging in a diagonal direction of 15° on an emulsion 10 μm thick while detecting reflection of Si 400, the degradation of resolution (i.e., blur) is on the order of 2.7 μm. Because the gap between the sample crystal 101 and the x-ray detection film 106 is kept to about 20 mm, the x-ray optical resolution is 10 μm. In contrast to this value, the value of 2.7 μm, which is effective for diagonal incidence, lies in the permissible range, and thus the resolution is adequate for practical purposes.

Where an imaging plate, which is a storage phosphor, is used instead of the x-ray detection film 106 as the x-ray detection element, the fact that the thickness of the sensing body corresponding to the thickness of the emulsion is 100 μm means that degradation of resolution due to diagonal incidence is on the order of 27 μm. The sensing resolution of the imaging plate is 50 μm, so the smaller image unsharpness of 27 μm is not considered a problem in practical terms.

However, theoretically, vertical incidence of the diffracted x-ray on the imaging plate is ideal for obtaining high resolution topographs.

In instances where a flat x-ray sensing film is used, in order to protect the x-ray film or imaging plate from the phenomenon of fogging due to scattered x-rays, it is necessary to make the width of the diffraction slit piece larger. However, in this case the diffraction slit piece becomes larger and heavier, and it is necessary for the component supporting it to be robust, which has at times led to the problem that the x-ray detection section inclusive of the x-ray detection film and the like is excessively large and heavy.

In the field of electrostatic transfer apparatuses, there are known apparatuses adapted to produce an electrostatic latent image on the surface of a rotating photosensor drum (for example, Japanese Laid-Open Patent Applications H05-289190 and H10-313383). According to this invention, a planar x-ray detector of greater surface area than the sample is deformed into a cylindrical shape, but this component is completely different from the photosensor drums used in electrostatic transfer apparatuses.

From the above it will be appreciated that conventional x-ray topography apparatuses have problems such as the following.

(1) When a flat and planar x-ray detector is used in an arrangement in which the diffracted x-ray is incident from a perpendicular direction (e.g., as in FIG. 9A), resolution of the x-ray topograph is lower in the section where the gap between the sample and the x-ray detector is wide. If the sample has a large diameter, the gap between the sample and the x-ray detector must be expanded further in order to avoid collision with the diffraction slit during scanning, thereby further exacerbating the drop in resolution.

(2) When a flat and planar x-ray detector is used in an arrangement in which the diffracted x-ray is incident from an oblique direction (e.g., as in FIG. 9B), resolution of the x-ray topograph is reduced by the obliquely incident x-rays.

(3) In the apparatus depicted in either FIG. 9A or FIG. 9B, when the sample is of a large diameter, the surface area of the planar x-ray detector must be larger as well, making the x-ray detection section larger and harder to manipulate.

SUMMARY OF THE INVENTION

With the foregoing in view, it is an object of the present invention to enable use of a planar x-ray detector of large surface area commensurate with the sample, even if the sample has a large diameter, without any reduction in resolution of the x-ray topograph.

It is a further object of the present invention to eliminate the need for the overall shape of the x-ray detection section to be increased in size, even when the planar x-ray detector used has a larger surface area commensurate with a larger diameter sample.

The x-ray topography apparatus according to the present invention provides an x-ray topography apparatus for detecting, using an x-ray detector, a linear x-ray diffracted from a sample to obtain a planar diffraction image when the sample is scanned with the x-ray, the x-ray topography apparatus comprising: the x-ray detector being a planar x-ray detector of cylindrical shape having a surface area greater than the surface area of the sample; detector rotation means for rotating the planar x-ray detector about a center axis of the cylindrical shape in coordination with a scanning movement of the linear x-ray; and the center axis of the cylindrical shape extending in a direction at a right angle to the direction of the scanning movement of the linear x-ray.

In preferred practice, this x-ray topography apparatus is an x-ray topography apparatus employing the Lang method, which is a transmissive and single crystal technique. The sample is a single crystal sample of Si (silicon) semiconductor having a circular disk shape having a diameter of for example 300 mm or more, for example 450 mm. In order to form a linear x-ray on the sample, typically a slit member is arranged in front of the sample. This linear x-ray may be transformed to a curved x-ray by adopting a curved shape for the slit of the slit member. Scanning of the sample with a linear x-ray is typically carried out with the linear x-ray fixed, by moving the sample with respect to the x-ray.

In the x-ray topography apparatus according to the present invention, preferably, the extension direction of the linear x-ray is a direction at a right angle to the direction of the scanning movement of the linear x-ray; and the center axis of the cylindrical shape of the planar x-ray detector extends parallel to the same direction as the extension direction of the linear x-ray. Through this configuration, the x-ray topograph of the sample may be formed on the planar x-ray detector, so as to have a geometrical 1(one)-to-1(one) relationship to the sample.

The extension direction of the linear x-ray refers, in the case of a linear x-ray of straight line shape, to the extension direction of that line; or in the case of a linear x-ray of curving shape, to the extension direction of a straight line connecting the two ends of the curved linear x-ray.

In the x-ray topography apparatus according to the present invention, preferably, the detector rotation means rotates the planar x-ray detector so that a peripheral speed of an external peripheral surface of the planar x-ray detector and a scanning movement speed of the linear x-ray are the same. Through this configuration, the x-ray topograph of the sample may be formed on the planar x-ray detector, so as to have a geometrical 1-to-1 relationship to the sample.

In the x-ray topography apparatus according to the present invention, the planar x-ray detector may have a cylindrical storage phosphor as a member irradiated with a diffracted x-ray from the sample. This storage phosphor is a substance that accumulates energy in a portion irradiated with the x-ray, and that releases the energy as light emission when the portion is irradiated with light. This storage phosphor is known by trade names such as an imaging plate.

In the x-ray topography apparatus according to the present invention, the planar x-ray detector may be disposed in a dark box, namely a camera obscura. A read device and an erase device may be provided around the planar x-ray detector in the dark box. The read device may be a device for reading an image stored in the planar x-ray detector. The erase device may be a device for erasing the image stored in the planar x-ray detector. According to this configuration, reading processes and erasing processes can be carried out on stored data without detaching the storage phosphor used as the planar x-ray detector from the x-ray topography apparatus, and a plurality of x-ray topographs may be acquired in succession.

In the x-ray topography apparatus according to the present invention, preferably, the planar x-ray detector is provided at a position in which an x-ray diffracted from the sample is incident from a normal direction to a cylindrical surface of the planar x-ray detector. According to this configuration, the width of the slit piece of the diffraction slit for preventing scattered x-rays from reaching the planar x-ray detector may be made as small as possible. Also, blur caused by oblique incidence of an x-ray is eliminated by causing the x-ray to be vertically incident, and the resolution of the x-ray topograph may be improved.

Preferably, the x-ray topography apparatus according to the present invention has a two-dimensional CCD sensor in which a plurality of CCD elements for receiving an x-ray and outputting a signal are arranged in a plane; and means for selectively placing either one of the planar x-ray detector and the two-dimensional CCD sensor at a position for detecting a diffracted x-ray from the sample. According to this configuration, measurement using the planar x-ray detector and measurement using the CCD sensor may be carried out selectively as needed. Typically, measurement using the CCD sensor yields a high resolution topograph, and thus measurement may be carried out by deriving an overall topograph using the planar x-ray detector, then making finer measurements of any localized areas for which more detailed information is desired, through measurement using the CCD sensor.

The x-ray topography apparatus of the present invention employing a CCD sensor may have CCD control means for controlling an operation of the plurality of CCD elements and determining an x-ray intensity on the basis of an output signal from each of the CCD elements; and the CCD control means may control the plurality of CCD elements on the basis of the TDI (time delay integration) method.

A control method by the TDI method refers to a readout method by the CCD sensor involving imaging an object that is moving at a constant speed, while bringing the movement direction and movement speed thereof and the charge transfer direction and the charge transfer speed in the CCD sensor into concordance. This method permits superimposed exposure of diffracted x-rays from the same location of a moving object onto the individual vertical lines of the CCD, and for this reason high sensitivity imaging can take place at high speed. The details of a CCD driving method that involves the TDI method are described in Japanese Laid-Open Patent Application 2006-071321, for example.

The method of controlling the CCD is not limited to the TDI method, and various other methods may be conceivable. For example, the frame acquisition method, which is the usual control method for acquiring images equivalent to single frames, is also acceptable. In the case of this method, an operation identical to the TDI operation may be accomplished through software. Specifically, a process whereby acquired frame images are overlapped and integrated while the images are shifted in synchronization with the scanning movement distance may be accomplished through software.

A CCD is used as the detector in the present application for reasons of ease of procurement and handling, but the detector is not limited to a CCD, and various other detectors may be used. Recent technological advances have led to the development of various types of two-dimensional detectors. Some of these two-dimensional detectors are known as "pixel detectors." Most of these pixel detectors are applications of semiconductor technology.

These pixel detectors have a number of advantages. For example, there have been developed photo-counting pixel detectors in which two-dimensional pixels are used and the individual pixels can be calculated at a high count rate; pixel detectors in which individual pixels are differentiated by energy; and the like. In the future, as pixel sizes decrease, such pixel detectors will have potential application in high resolution topography.

According to the present invention, because an x-ray topograph is captured while a planar x-ray detector of cylindrical shape is caused to rotate, even if the planar x-ray detector has a large surface area to correspond with the large diameter of a sample, a small gap may be maintained between the sample and the planar x-ray detector, and for this reason a planar x-ray detector of large surface area may be used with no reduction in the resolution of the x-ray topograph.

Moreover, according to the present invention, because an x-ray topograph is captured while a planar x-ray detector of cylindrical shape is caused to rotate, the x-ray detection section does not need to have a large overall shape even if the planar x-ray detector has a large surface area to correspond with the large diameter of a sample.

DETAILED DESCRIPTION OF THE PREFERRED EMBODIMENTS

The x-ray topography apparatus according to the present invention is described hereinbelow on the basis of a preferred embodiment. The x-ray topography apparatus of the present embodiment is used to obtain an x-ray topograph of a single crystal material such as a large-diameter (for example, about 450 mm) Si semiconductor wafer, for the purpose of inspecting the wafer for defects.

This embodiment should not be construed as limiting the present invention. While reference is made to the drawings in the description hereinbelow, in some instances structural elements are depicted in the drawings with proportions different from their actual ones, in order to facilitate understanding of specific sections.

(Goniometer)

Figure 1:
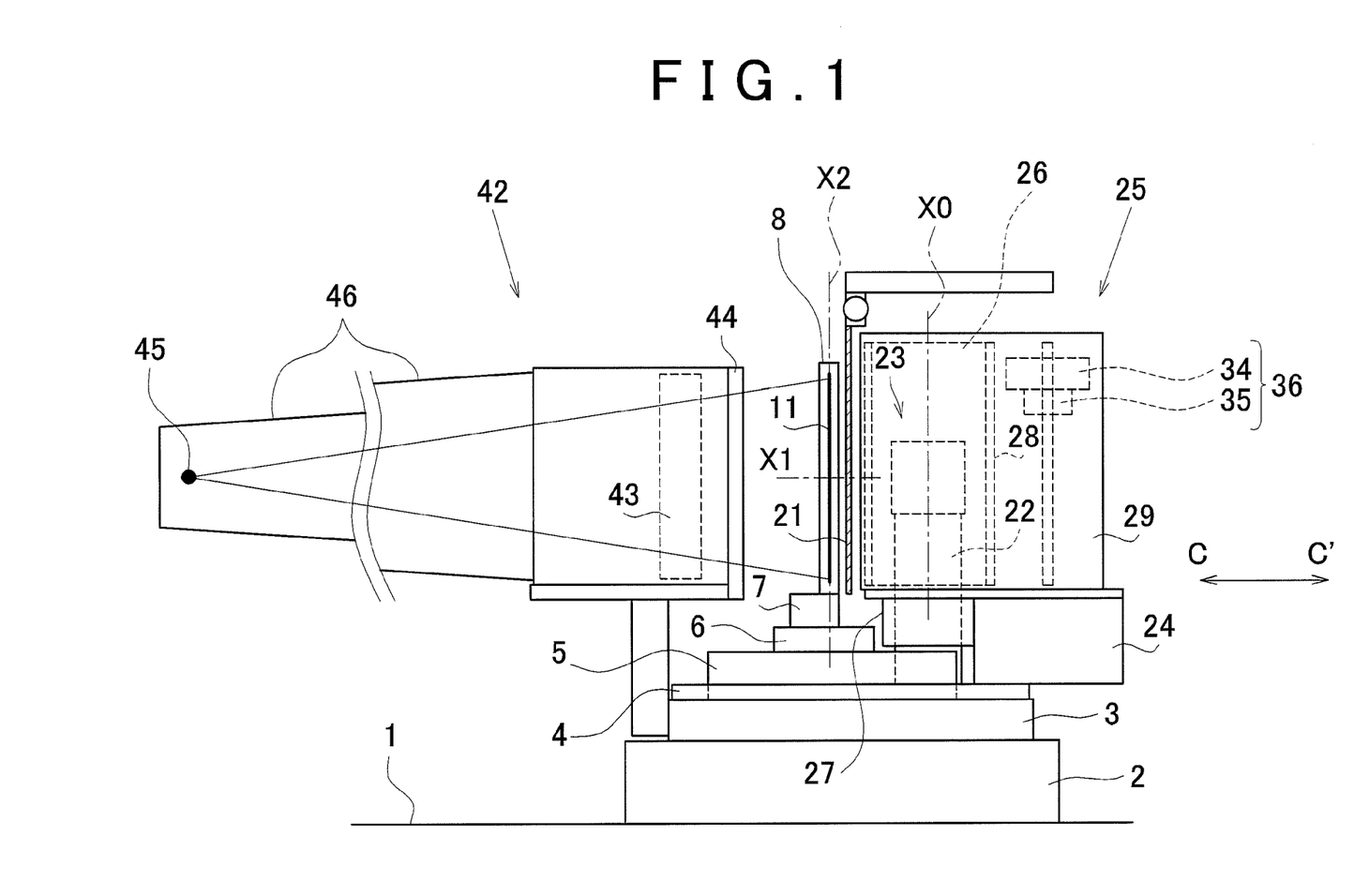
FIG. 1 is a front view of an embodiment of the x-ray topography apparatus according to the present invention.
Figure 2:
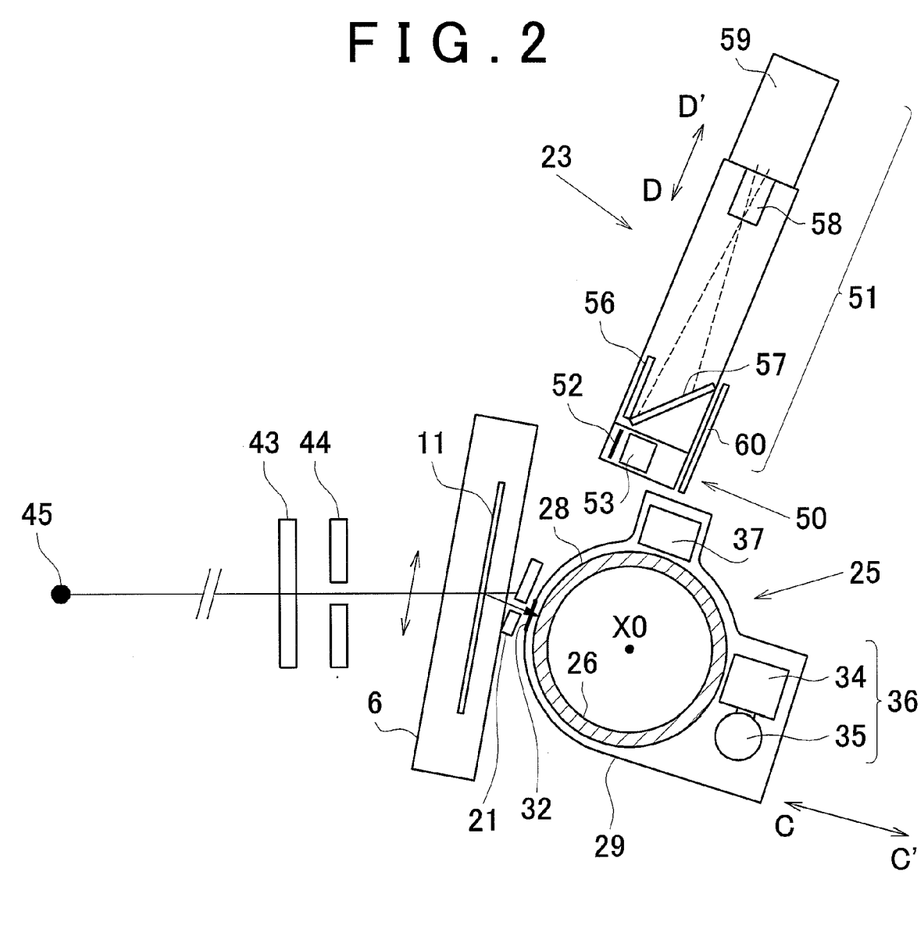
FIG. 2 is a plan view of the x-ray topography apparatus of FIG. 1, and shows conditions during imaging plate measurement.

FIG. 1 shows a front view structure of the x-ray topography apparatus according to the present embodiment. FIG. 2 shows a plan view structure of the same x-ray topography apparatus. In FIG. 2, some constitutional elements have been omitted for convenience. The x-ray topography apparatus of the present embodiment is an x-ray topography apparatus based on the exclusively transmissive Lang method. In FIG. 1 and FIG. 2, a mount 2 is immovably fixed to a base surface 1 such as a floor, and a base 3 is immovably fixed to the mount 2. The height of the upper face of the base 3 is adjustable in relation to the mount 2. The upper face of the base 3 is horizontally adjustable.

A 2θ-rotation platform 4 is provided on the base 3. A ω-rotation platform 5 is provided on the base 3, in a coaxial positional relationship with the 2θ-rotation platform 4. A scanning stage 6 is provided on the ω-rotation platform 5. A φ rotation device 7 is provided on the scanning stage 6. The φ rotation device 7 supports a sample holder 8. The sample holder 8 can be detachably attached to the φ rotation device 7 by a manual operation. A sample crystal 11 is immovably housed, i.e., attached, within the sample holder 8.

The φ rotation device 7 rotates the sample holder 8 about an axis X1 that corresponds to the center axis of the sample crystal 11 attached to the sample holder 8; i.e., performs so-called intra-planar rotation. This intra-planar rotation is carried out for the purpose of adjusting the angle of the lattice plane of the sample crystal 11 with respect to an x-ray incident on the sample crystal 11.

Through electrical actuation, the scanning stage 6 moves and gives rise to reciprocating linear movement within a horizontal plane by the φ rotation device 7 which supports the sample holder 8. The scanning stage 6 undergoes electrically actuated movement within a range of ±250 mm, for example. Due to this parallel movement of the scanning stage 6, an x-ray of curved linear shape passing through a curved slit 44, discussed later, is scanned over the measured face, i.e., the sample face, of the sample crystal 11. Also, the location at which an x-ray strikes the sample crystal 11 may be adjusted to a desired location through parallel movement of the scanning stage 6.

The ω-rotation platform 5 rotates the scanning stage 6, which supports the sample holder 8 and the φ rotation device 7, about an axis X2 at a right angle to the center axis X1 of intra-planar rotation. This rotation is termed ω-rotation, and is carried out for the purpose of varying the incidence angle of an x-ray onto the sample crystal 11. The ω-rotation allows both rough setting and fine setting through electrical actuation in a tangent bar system.

Figure 7:
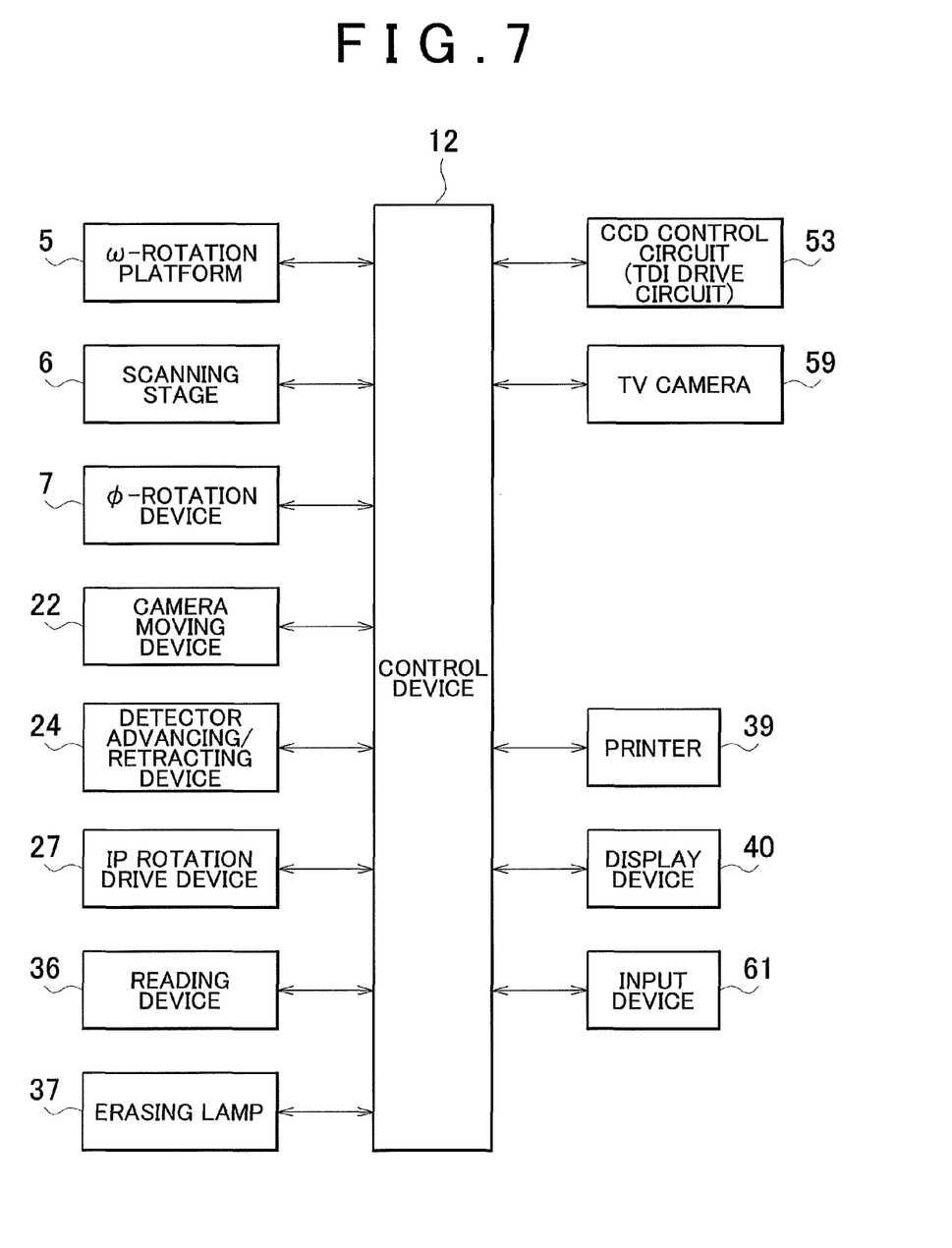
FIG. 7 is a block diagram showing an example of a configuration of a control system of the x-ray topography apparatus of FIG. 1.

The respective operations of the ω-rotation platform 5, the scanning stage 6, and the φ rotation device 7 are controlled by a control device 12 of FIG. 7. The control device 12 is, for example, composed of a control circuit that includes a computer. The computer includes a memory, and in the memory there is stored program software for the purpose of prompting the components that make up the x-ray topography apparatus to perform a series of operation in order to obtain an x-ray topograph using the x-ray topography apparatus. The ω-rotation platform 5, the scanning stage 6, and the φ rotation device 7 function in accordance with this program software.

(Sample Holder)

Figure 4:
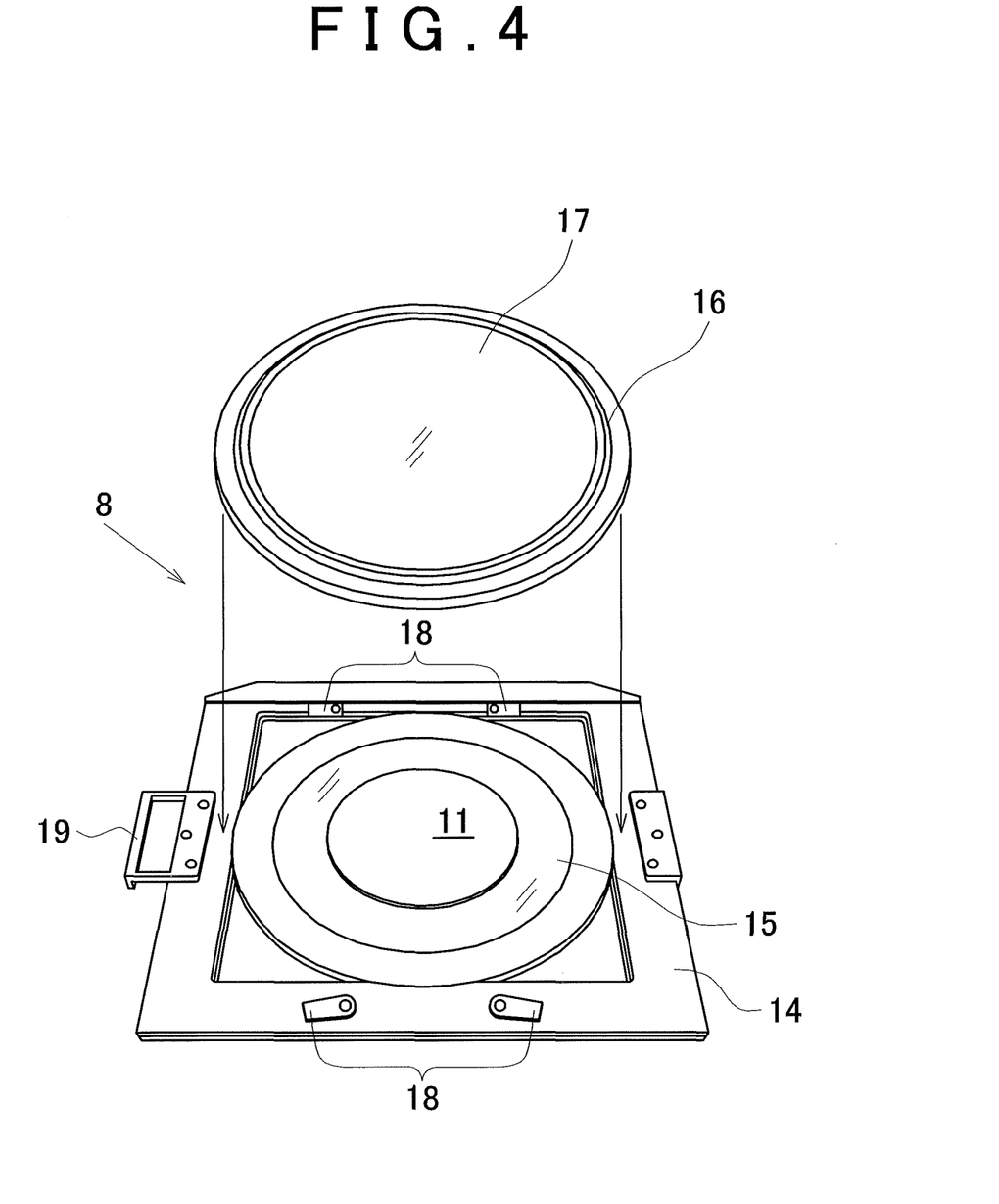
FIG. 4 is an exploded perspective view showing an example of a sample holder.

The sample holder 8 is assembled as shown in FIG. 4, for example, by sandwiching the sample crystal 11 between a high strength film 15 provided over a holder substrate 14 and a high strength film 17 provided about the entire circumference of a cover ring 16, and then fastening the cover ring 16 to the holder substrate 14 by a clamp member 18. The operator holds the sample holder 8 by gripping a grip handle 19, and carries the holder to the θ rotation device 7 of FIG. 1 where the holder is installed.

(2θ-rotation Platform)

The 2θ-rotation platform 4 supports a diffraction slit 21 situated to the rear of the sample crystal 11, a camera-moving device 22 situated to the rear of the diffraction slit 21, and a detector advancing/retracting device 24 situated to the rear of the camera-moving device 22. A television unit 23 for setting is supported by the camera-moving device 22. The detector advancing/retracting device 24 supports a detector unit 25 and an IP rotation drive device 27.

The 2θ-rotation platform 4 is capable of rotating about the axis X2, which passes in the vertical direction through the sample face of the sample crystal 11. Due to this rotation, the detector advancing/retracting device 24, the IP rotation drive device 27, the detector unit 25, the diffraction slit 21, and the settings television unit 23, which are supported on the 2θ-rotation platform 4, may be rotated in their entirety in unison about the axis X2 which passes through the sample crystal 11. This rotation is for adjusting the angle of an imaging plate 28, which is housed within the detector unit 25, with respect to the sample crystal 11, and is referred to as 2θ-rotation. 2θ-rotation is set by scale marks and a pointer. Ideally, the axis X2 for ω-rotation and the axis X2 for 2θ-rotation would be completely coincident axes, but a slight difference is tolerable within a permissible range for practical purposes, to reflect component error and mechanism assembly error.

A rotation drum 26 and the imaging plate 28 that is wound around the rotation drum 26 (e.g., by adhesion) are housed inside the detector unit 25. The rotation drum 26 is driven by IP rotation drive device 27, to rotate about a center axis X0. The imaging plate 28 rotates in unison with the rotation drum 26. In the present embodiment, this rotation of the imaging plate 28 is referred to as α rotation. In development view, the imaging plate 28 is rectangular or square, and the surface area thereof is of a size able to contain the entire sample crystal 11.

α-Rotation is controlled by the control device 12 of FIG. 7, for example, in the following manner. Specifically, when a topograph is captured, a rotation proceeds at low speed and is synchronized with movement of the scanning stage 6; during a read process, α rotation proceeds at high speed; and during an erase process, α rotation is one rotation at low speed. The control device 12 controls linear reciprocating movement of the sample crystal 11 by the scanning stage 6, the α rotation of the imaging plate 28, the height varying movement of a height limiting slit 43 and the ω-rotation of the ω-rotation platform 5 so that these are coupled with one another.

Figure 5:
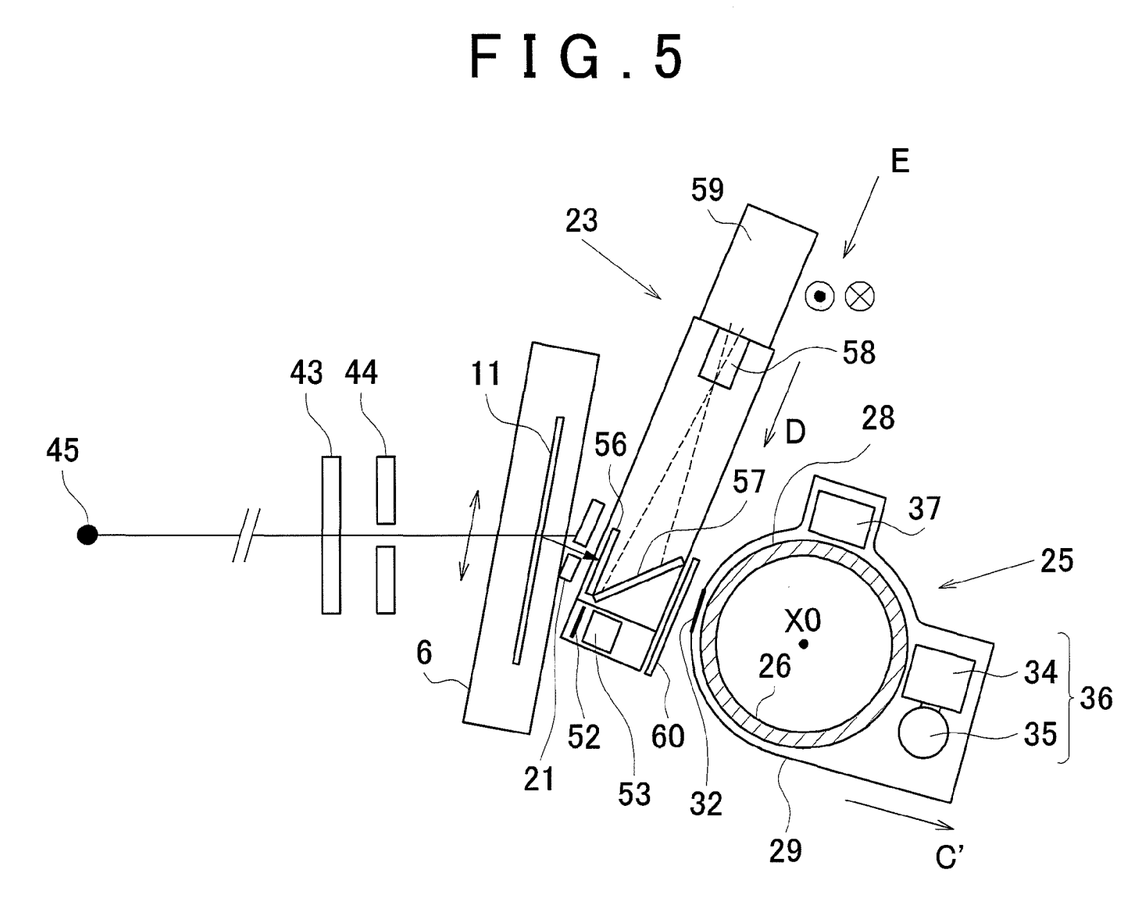
FIG. 5 is a plan view of the x-ray topography apparatus of FIG. 1, and is a drawing showing conditions during camera imaging.

As shown by arrows C-C' in FIG. 2, the detector advancing/retracting device 24 advances and retracts the entire detector unit 25 in the approximately perpendicular direction in relation to the diffraction slit 21. FIG. 2 depicts a state in which the detector unit 25 is performing an advancing movement in the direction of arrow C, and FIG. 5 depicts a state in which the unit is performing a retracting movement in the direction of arrow C'.

As shown by arrows D-D' in FIG. 2, the camera-moving device 22 causes the entire settings television unit 23 to move in an advancing or retracting manner in a direction that is approximately parallel to the diffraction slit 21. FIG. 2 depicts a state in which the device is performing a retracting movement in the direction of arrow D', and FIG. 5 depicts a state in which the device is performing an advancing movement in the direction of arrow D.

A two-dimensional CCD sensor 52 and a fluorescent plate 56 are provided inside the television unit 23. The camera-moving device 22 and the detector advancing/retracting device 24 function as means for selectively positioning the imaging plate 28, the two-dimensional CCD sensor 52, or the fluorescent plate 56 at a location to detect an x-ray from the sample crystal 11. In FIG. 7, the camera-moving device 22 and the detector advancing/retracting device 24 operate according to program software stored in the memory of the control device 12.

(Detector Unit)

In FIG. 1 and FIG. 2, the detector unit 25 has a dark box, namely a camera obscura 29 that is supported on a detector advancing/retracting device 24. A cylindrical rotation drum 26 is provided in the dark box 29, and the imaging plate 28 is wound around the external circumferential surface of the rotation drum 26, thus forming a cylindrical shape. The imaging plate 28 is formed from a sheet-form storage phosphor having a predetermined thickness. An incident x-ray window 32 formed from a material that allows x-rays to pass through, such as a black paper, is provided on the part of the dark box 29 that is opposite the diffraction slit 21.

The dark box 29 is formed, for example, from a metal such as stainless steel, and prevents the imaging plate 28 from being exposed by scattered x-rays. The back surface of the dark box 29 may be plastic.

The rotation drum 26 and the imaging plate 28 are driven by the IP rotation drive device 27 shown in FIG. 1 so as to rotate about the center axis XO. A reading device 36 and an erasing lamp 37 are provided at the periphery of the imaging plate 28 in the dark box 29. The reading device 36 has a reading head 34 and a head raising/lowering device 35.

Operation of the IP rotation drive device 27, the reading device 36, and the erasing lamp 37 are controlled by the control device 12 shown in FIG. 7. A printer 39 and an image display device 40 are connected to the output port of the control device 12. Reading is carried out every 50 μm, for example. The resulting data that has been read by the reading device 36 is subjected to predetermined data processing using programming software and is visualized as an x-ray topograph by the printer 39 and the image display device 40.

(Incident-side Optical System)

In FIG. 1, an incident slit portion 42 is supported by the base 3. The height limiting slit 43 and the curved slit 44 for limiting width of x-rays are provided inside the incident slit portion 42. The slit length in the height direction of the height limiting slit 43 can be adjusted by the control device 12 shown in FIG. 7. Details concerning the height limiting slit 43 and the curved slit 44 are described, for example, in Japanese Laid-open Patent Publication No. H11-014564.

An x-ray source 45 is provided above the base surface 1 set apart from the mount 2. The space between the x-ray source 45 and the incident slit portion 42 is covered by a shielding member 46, and an x-ray path is formed in this covered section. In the present embodiment, the x-ray path is not evacuated to a vacuum but it may be evacuated to a vacuum, as necessary. The x-ray source 45 has a configuration in which it contains a cathode such as a filament or the like and an anode such as a rotary target or the like. The anode is formed, for example, from Mo (molybdenum), and x-rays containing characteristic x-rays of MoKα are discharged from the anode.

Known methods for taking x-rays emitted by the anode to the outside include a method of taking them out in the form of point-focus x-rays and a method of taking them out in the form of line-focus x-rays. Point-focus x-rays have a practically square or circular cross section, while Line-focus x-rays have a rectangular cross section. In the present embodiment, x-rays are taken to the outside in the form of point-focus.

(Television Unit for Setting and Camera Movement Device)

In FIG. 2, the television unit 23 for setting has a TDI/CCD unit 50 at the forward end thereof, and a TV camera unit 51 at the rear part thereof. The TDI/CCD unit 50 has a two-dimensional CCD sensor 52 formed from a plurality of CCD (charge-coupled device) elements that directly receive x-rays and are aligned horizontally, and a CCD control circuit 53 that contains the TDI drive circuit for operating this two-dimensional CCD sensor in a TDI (time delay integration) manner. The output signal from each of the CCD elements can be taken off from an output terminal of the CCD control circuit 53.

The two-dimensional CCD sensor 52 is disposed so that the x-ray receiving surface is opposite to the sample crystal 11. The plane size of the x-ray receiving surface of the two-dimensional CCD sensor is, for example, 10×10 mm, and the number of CCD terminals contained therein, namely the pixel number, is 1024×1024, for example. The driving method of TDI type is a CCD reading method whereby an image of an object that is moving at a constant speed is taken by matching the speed direction of its movement with the CCD charge transport direction and transport speed. This method allows superimposed exposure of diffracted x-rays from the same location of a moving object on the individual vertical lines of the CCD. This allows high-sensitivity imaging to be carried out, even at high speeds. Details concerning a CCD drive method of TDI type are described, for example, in Japanese Laid-open Patent Publication No. 2006-071321.

The TV camera unit 51 has a fluorescent plate 56 that converts x-ray images into light images, a reflective mirror 57 disposed behind the fluorescent plate 56, a lens 58 disposed on the light path of the light reflected by the reflective mirror 57, and a television camera 59 that takes a reflected image of the reflective mirror 57. The reflective mirror 57 has the action of altering the light path by 90°. The lens 58 forms images on the imaging surface of the television camera 59 based on the light image reflected at the reflective mirror 57.

A shielding plate 60 is provided behind the forward end portion of the settings television unit 23. The shielding plate 60 is attached at a suitable location on the camera moving device 22. This shielding plate 60 prevents diffracted x-rays from being incident on the imaging plate 28 during the various adjustment processes carried out using the television camera 59 (see FIG. 5). The size of the shielding plate 60 is large enough to shield the imaging plate 28 from being irradiated with x-rays which pass through the incident x-ray window 32. For example, the width of the shielding plate 60 is about 100 mm, and the height is about 600 mm, which is greater than the 500 mm sensing height of the imaging plate 28. In addition, the shielding plate 60 is thick enough to shield diffracted x-rays, for example, a thickness of 2 to 3 mm for brass.

The video signal of the television camera 59 is subjected to the requisite processing by the control device 12 in FIG. 7 and is then transmitted to the signal input terminal of the image display device 40. The image that has been formed on the fluorescent plate 56 is reflected by the reflective mirror 57, passed through a lens 58, imaged by the television camera 59, and displayed on the screen of the image display device 40, as necessary. When reflected by the reflective mirror 57, the image undergoes left-right transposition. In order to undo this transposition, image transposition may be carried out again using a reflective mirror, or processing such as left-right transposition of the image frame data may be carried out during the image signal processing procedure.

As described in relation to FIG. 1, the settings television unit 23 is driven by the camera moving device 22 and is made to advance or retract with respect to the diffraction slit 21. Specifically, the settings television unit 23 moves in parallel with a horizontal plane between the retracted position shown in FIG. 2, the television imaging position shown in FIG. 5, and the CCD image-capturing position shown in FIG. 6.

Figure 6:
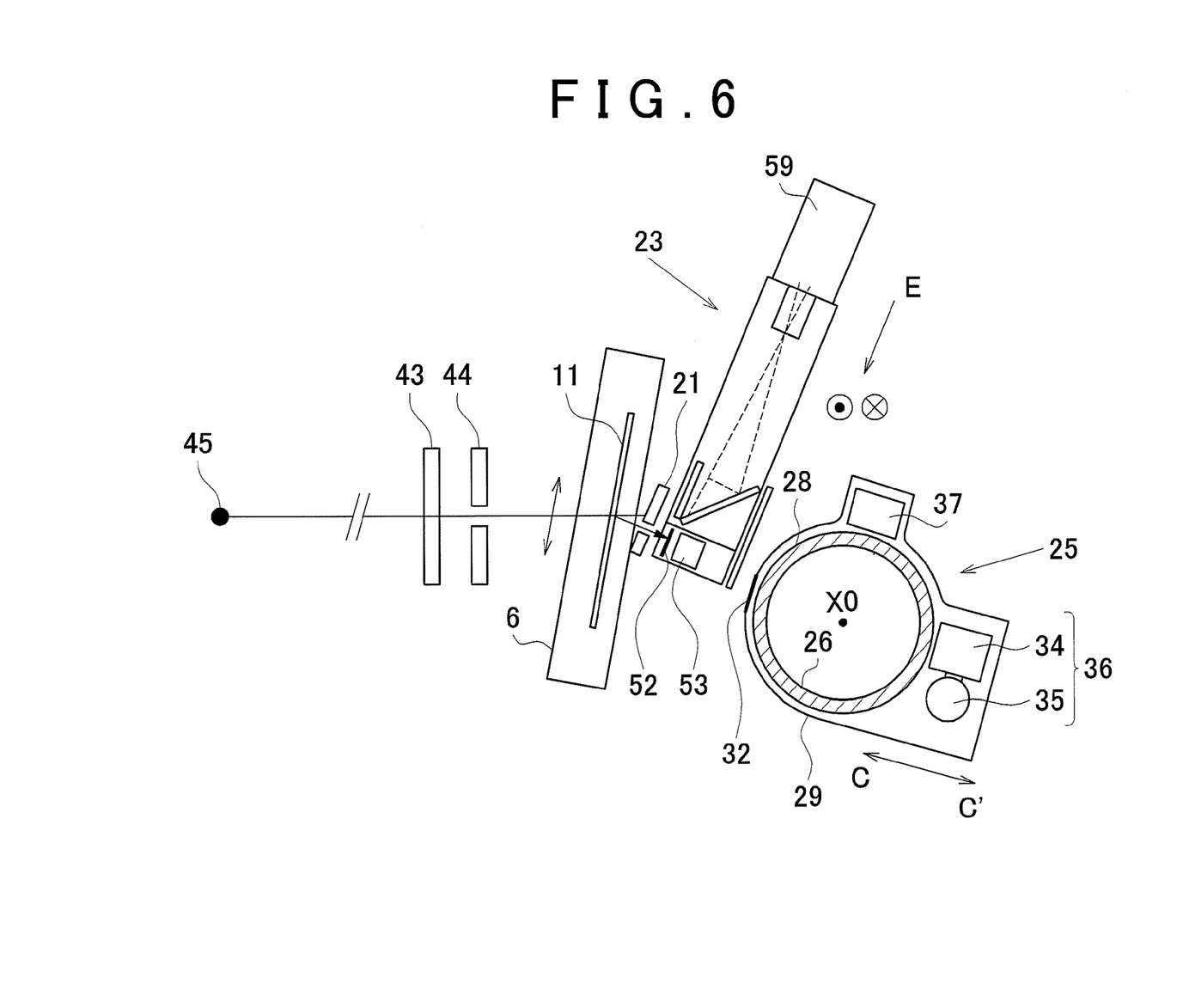
FIG. 6 is a plan view of the x-ray topography apparatus of FIG. 1, and is a drawing showing conditions during CCD imaging.

The retracted position shown in FIG. 2 is a position at which there will be no impediment to positioning of the imaging plate 28 at the predetermined x-ray receiving position in the vicinity of the diffraction slit 21. The television imaging position of FIG. 5 is a position behind the diffraction slit 21 at which the fluorescent plate 56 receives the diffracted x-rays that have passed through the diffraction slit 21. The CCD image-capturing position of FIG. 6 is a position behind the diffraction slit 21 at which the two-dimensional CCD sensor 52 receives diffracted x-rays that have passed through the diffraction slit 21.

The field of view of the television camera 59 is about 100 mm in the height direction. Because the diffracted image from the sample crystal 11 having a diameter of 450 mm is observed over the entire range in the vertical direction, the camera moving device 22 causes the settings television unit 23 to perform a parallel movement in the upwards/downwards direction (namely, vertical direction) as indicated by the symbol E in FIG. 5, specifically, a raising/lowering movement. Because the width of the diffracted x-rays is 1 mm, the television camera 59 needs to have the field of view covering about 20 mm in the widthwise direction, in consideration of the several millimeters of curving of the diffracted x-rays.

(Description of the Optical System)

Figure 3A:
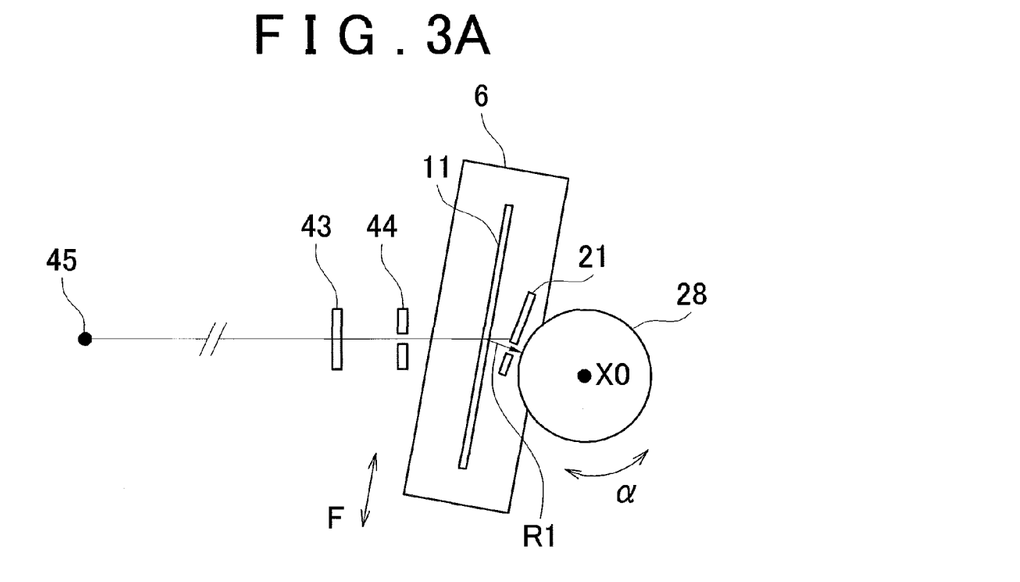
FIG. 3A is a plan view showing an optical system of the x-ray topography apparatus of FIG. 1.
Figure 3B:
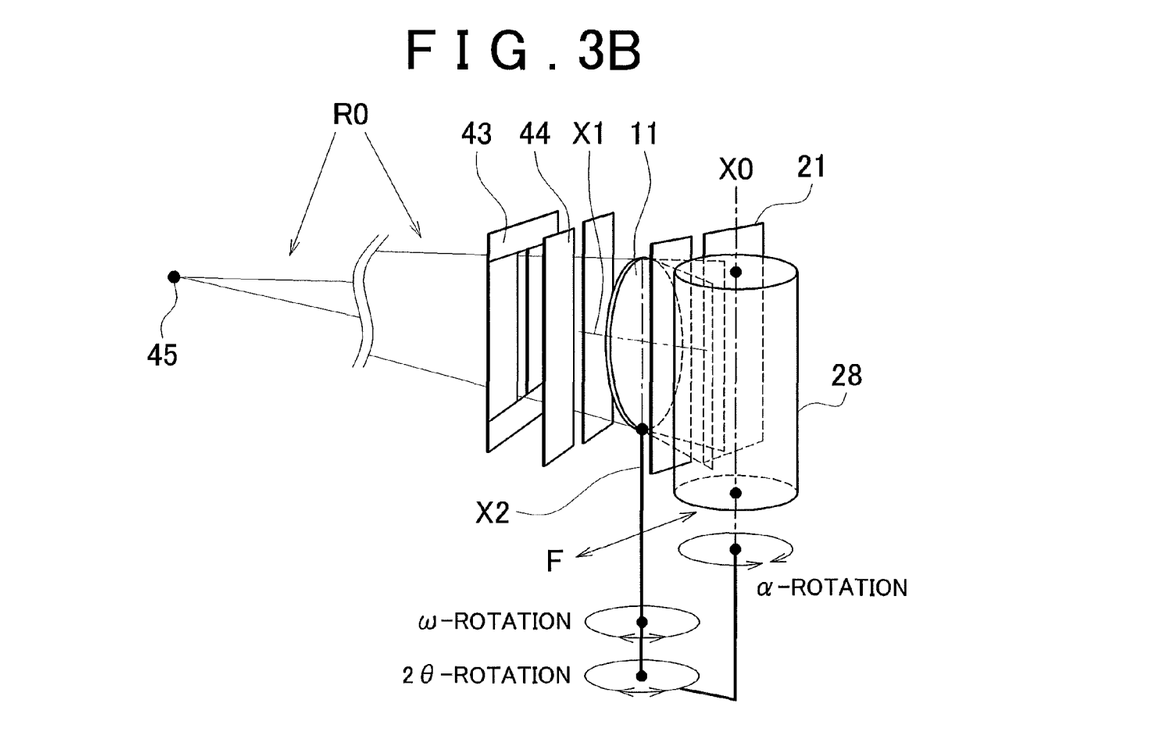
FIG. 3B is a perspective view showing an optical system of the x-ray topography apparatus of FIG. 1.

FIG. 3A and 3B are simplified views of the x-ray optical system of the x-ray topography device of FIG. 1. In the drawings, the goniometer has a two-axis configuration with ω-rotation and 2θ-rotation. Point-focus x-rays R0 taken out from the x-ray source 45 and having a practically square or circular cross section is restricted by the curved slit portion of the curved slit 44. Though the slit portion of the slit 44 is illustrated linearly in FIG. 3B, the slit portion actually curves. However, the slit portion of the slit 44 may be actually formed linearly. Specifically, in the horizontal direction, x-rays R0 are controlled with regard to their traveling direction, are restricted with regard to their width, and are then incident on the sample crystal 11. On the other hand, in the vertical direction, x-rays R0 become divergent x-rays and are incident on the sample crystal 11. Consequently, the incident x-rays irradiate a band-shaped region of the sample crystal 11. This region is referred to as the field of irradiation. The distance between the x-ray source 45 and the sample crystal 11 is about 2250 mm, for example, in consideration of the fact that the diameter of the sample crystal 11 is 450 mm.

When the rotation in the crystal plane and the x-ray incidence angle (namely, ω angle) are adjusted with respect to the incident x-rays R0 so that diffraction conditions are satisfied at the lattice plane of the sample crystal 11, the x-rays will satisfy the Bragg condition over the entire range of the field of irradiation, and diffraction will take place. In the present embodiment, the conditions are set so that the MoKα rays diffracts at the lattice plane of the sample.

The diffraction slit 21 shields the primary x-rays that have passed through the sample crystal 11 and also the slit width is constricted so that only the diffracted x-rays pass through. The background due to scattered x-rays is decreased as a result of the action of this diffraction slit 21. The diffracted x-rays are incident on the outer circumferential surface of the cylindrical imaging plate 28 and are recorded as a potential image. The imaging plate 28 is driven by the IP rotation drive device 27 of FIG. 1 to rotate in a manner of α-rotation on a 2θ-rotation system.

The scanning movement F of the sample crystal 11 by the scanning stage 6 is a reciprocal movement in which moving direction reverses at both ends of the sample crystal 11. The imaging plate 28 reciprocally moves synchronously with the scanning movement F of the sample crystal 11. In other words, the imaging plate 28 reciprocally moves at the same circumferential speed and in the same direction as the sample crystal 11. Reciprocal movement of the imaging plate 28 is effected by α-rotation of the imaging plate 28 around its own center axis XO. The α-rotation is repetitive, reciprocal and rotational motion that is synchronized with the scanning movement F.

Taking the radius of the outer circumferential surface of the imaging plate 28 as "r", if the imaging plate 28 is rotated at a rotational angle Δα with respect to the moving amount ΔX of the sample crystal 11 such that ΔX=r·Δα, then it is possible to record an x-ray diffraction image (specifically, a topograph) on the surface of the imaging plate 28 with the same dimension as the diameter of the sample crystal 11.

If the moving amount X of the sample crystal 11 is 500 mm, then, in order to image a topograph in one rotation of angle α (360°), the diameter of the imaging plate 28 will be r=79.577 mm. When the diameter of the imaging plate 28 becomes greater than this value, the width of the topograph becomes greater than the diameter of the sample crystal 11. For example, when the imaging plate is produced at r=80 mm, then an image is captured at a width of 452.38 mm when X=450 mm.

With x-ray topography using the Lang method, the vertical dimension of the topograph is slightly larger than the sample size. This is because the incident x-rays diverge in the vertical direction, and the diffracted x-rays also similarly diverge. Specifically, the value increases in accordance with the ratio of the distance between the x-ray source 45 and the imaging plate 28, and the distance between the x-ray source 45 and the sample crystal 11. More specifically, the topograph becomes ellipsoid in the vertical direction.

When measuring a sample crystal 11 having a diameter of 450 mm, the distance between the sample crystal 11 and the diffraction slit 21 is set to a suitable value of about 15 to 35 mm. In addition, the distance between the sample crystal 11 and the imaging plate 28 is set to a suitable value of about 20 to 40 mm. When determining the respective distances above, the distances are held constant during measurement.

Distortion of the topograph can be mitigated by adjusting the diameter "r" of the imaging plate 28. In principle, this is the same as adjusting the rotation speed of the imaging plate 28. An image viewed from the back surface of the sample crystal 11 is recorded on the imaging plate 28. Consequently, it is preferable to use the control device 12 of FIG. 7 or the reading device 36 of FIG. 2 in order to carry out image processing involving right-left transposition on the image data read from the imaging plate 28.

In FIG. 3A, the diffraction slit 21 is disposed vertically with respect to the diffraction x-rays R1. As a result, the width of the slit piece of the diffraction slit 21 that forms a slit opening can be set at the required minimum width.

α-Rotation of the cylindrical imaging plate 28 has the dual function of rotation for topograph capture and rotation for reading the data that has been captured. The entire stored image can be read by the reading head 34 by moving the reading head 34 upwards and downwards using the head raising/lowering device 35 of FIG. 2 during α-rotation of the imaging plate 28 subsequent to image formation. In addition, the stored data over the entire surface of the imaging plate 28 can be erased by irradiating the imaging plate 28 with light from the erasing lamp 37 after reading processing.

α-Rotation of the imaging plate 28 involves low-speed rotation during topograph capture and high-speed rotation during reading. This α-rotation of the imaging plate 28 is produced by the IP rotation drive device 27 of FIG. 1. Regarding the detailed configuration of the IP rotation drive device 27, a suitable configuration may be used in accordance with requirements. For example, feedback control can be carried out using an electrical motor, thus allowing the rotation speed to be controlled, or a scanning motor and a reading motor can be provided separately, and utilization of the motors can be switched.

(X-ray Topograph Measurement Operation)

Figure 8:
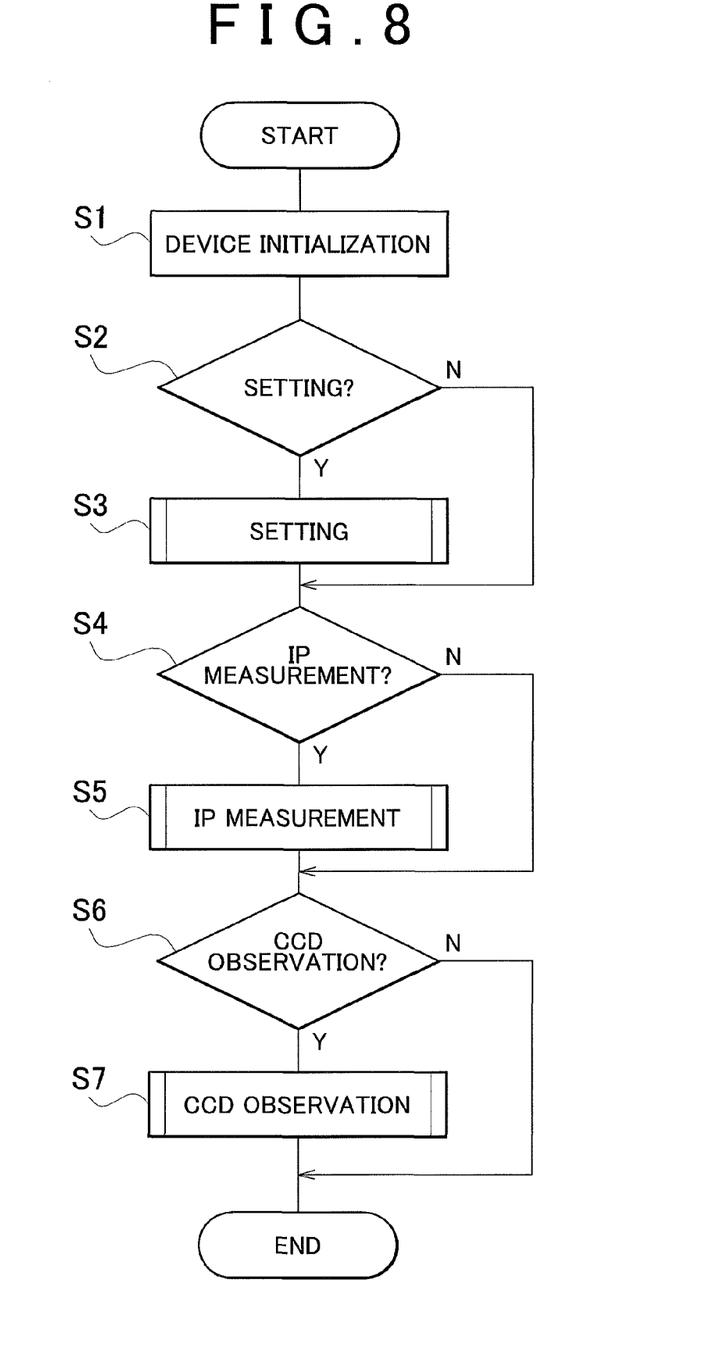
FIG. 8 is a flowchart depicting a flow of control carried out by the control system of FIG. 7.

With the control device 12 of FIG. 7, the various configurational parameters of the x-ray topography device are set at predetermined initial values as shown, for example, in the flow chart of FIG. 8 (step S1). Next, the respective processes of setting (steps S2, S3), IP measurement (steps S4, S5) and CCD observation (steps S6, S7) are carried out as necessary. Whether or not to carry out each process is determined by the measurement operator who operates an input device 61 of FIG. 7, such as a keyboard, mouse, or touch panel.

(Setting Process)

The setting process is one in which an image of the sample crystal 11 obtained using the television camera 59 in the state shown in FIG. 5 is observed, the crystal is centered, the width of the diffraction slit is set, the crystal ends are detected, the curving correction data is set, and other parameters are adjusted.

When the setting process is selected, the detector unit 25 in FIG. 2 is moved backward in the direction indicated by the arrow C', thereby moving it to the retracted position shown in FIG. 5. Next, the settings television unit 23 is moved forward in the direction of arrow D, thereby moving it to the television capture position shown in FIG. 5.

In this state, the x-rays are received by the fluorescent plate 56 as the settings television unit 23 is raised and lowered as indicated by the arrow E, and a fluorescent image is formed. Next, this fluorescent image is captured by the television camera 59, and the resulting captured image is observed on the display, allowing various adjustments of the x-ray topography device to be made.

(Measurement Using the Imaging Plate)

Subsequently, the settings television unit 23 is retracted to the retracted position shown in FIG. 2, and a space is formed in the rearward portion of the diffraction slit 21. The imaging plate 28 is moved along with the detector unit 25 into this space. The distance between the sample crystal 11 and the imaging plate 28 is set to a preset value at a prescribed location in memory, and the imaging plate 28 is automatically disposed at the predetermined position. The preset value can be altered to a desired value.

When the imaging plate 28 is at the measurement position shown in FIG. 2, topography capture on the imaging plate 28 is carried out. Specifically, the sample crystal 11 is first moved parallel to the sample surface by the scanning stage 6, and the sample surface of the sample crystal 11 is scanned with linear x-rays that are formed by the curved slit 44. The cylindrical imaging plate 28 is caused to rotate about the center axis XO by the IP rotation drive device 27 of FIG. 1 in synchronization with scanning movement of the sample 11; i.e., at the same circumferential speed and in the same direction. As a result, a diffraction image (specifically, a topograph) of the entirety of the sample crystal 11 is recorded as a planar image with a 1:1 geometrical positional relationship on the surface of the imaging plate 28.

Next, when the imaging plate 28 is placed at the retracted position shown in FIG. 5 or FIG. 6, the reading process is carried out on the stored image using the reading device 36, and the erasing process is carried out on the stored image using the erasing lamp 37. When the reading process is carried out on the imaging plate 28, the sample crystal 11 may be exchanged, or centering and other adjustments may be carried out using the settings television unit 23.

(CCD Observation)

A topograph image of the entirety of the sample crystal 11 is obtained using the imaging plate 28, and when a noteworthy defect image is produced while this topograph image is viewed, the vicinity of the defect image can be identified, and high-resolution observation can be carried out using the CCD sensor 52. In this case, as shown in FIG. 6, the settings television unit 23 is placed in the CCD imaging position. Next, based on the results of measurement of the imaging plate 28 carried out in advance, the desired measurement locations are designated, and the desired measurement position of the sample crystal 11 is moved to the observation position by raising or lowering as indicated by the arrow E and by planar movement using the scanning stage 6 of FIG. 1.

Because the sample crystal 11 is imaged by the CCD sensor 52 using a TDI system in this embodiment, a resolution of 25 μm or less can be sought. It is accordingly possible to discover fine defects that are impossible to capture by measurements using the imaging plate 28.

With the conventional device shown in FIG. 9A, in order to prevent image blurring due to oblique incidence of x-rays, the sample crystal 101 and the x-ray detection film 106 are oriented at an angle with respect to each other, whereby the diffracted x-rays from the sample crystal 101 are caused to be incident on the x-ray detection film 106 at a right angle. As a result, however, the gap at one end of the sample crystal 101 and the x-ray detection film 106 widens, and there have been problems with lowered resolution in this section. In particular, when the diameter of the sample crystal 101 is large, i.e., 450 mm, the gap at one end becomes extremely large, and the decrease in resolution has accordingly been dramatic.

As a countermeasure, in this embodiment, an x-ray topograph of the sample crystal 11 was taken by rotation of the cylindrical imaging plate 28. Consequently, the gap between the sample crystal 11 and the imaging plate 28 can always be kept constant over the entire surface of the imaging plate 28, even when the diffracted x-rays from the sample crystal 11 are made to be incident at a right angle to the imaging plate 28, specifically, at a right angle with respect to a tangent of the imaging plate 28. For this reason, it is possible to obtain a topograph of fixed resolution on the imaging plate 28. Moreover, since the x-rays are always incident at a right angle to the imaging plate 28, there is no blurring such as is seen during oblique incidence, allowing a high-resolution image to be obtained.

Moreover, in this embodiment, the imaging plate 28 has a cylindrical shape, and thus the scattered x-rays can be prevented from reaching the imaging plate 28, although the width dimension of the slit piece of the diffraction slit 21 is extremely small. The fact that the width of the slit piece of the diffraction slit 21 can be reduced means that the diffraction slit 21 and the sample crystal 11 undergoing scanning movement can be prevented from colliding with each other even when the gap between the sample crystal 11 and the diffraction slit 21 is narrow.

The fact that the gap between the sample crystal 11 and the diffraction slit 21 or, in other words, the gap between the sample crystal 11 and the imaging plate 28, can be narrow ultimately means that it is possible to obtain a high-resolution x-ray topograph.

As described above, in accordance with this embodiment, an x-ray topograph can be obtained having consistently high resolution over its entirety, without any blur caused by oblique incidence of x-rays.

The present invention also includes a technique whereby the diffracted x-rays from the sample crystal 11 are made incident on the imaging plate 28 from an oblique direction; however, the resolution is improved in this case as well, because the gap between the sample crystal 11 and the imaging plate 28 is reduced, and more uniform resolution is obtained because the gap between the sample crystal 11 and the imaging plate 28 is constant over the entire imaging plate 28.

(Additional Embodiments)

A preferred embodiment was cited above to describe the present invention, but the present invention is not limited to this embodiment, and it is possible to make a variety of modifications that remain within the scope of the invention as defined by the patent claims.

For example, the present invention was used in the above embodiment employing the Lang method, which is a transmissive and single crystal method. However, the present invention may also be utilized with x-ray topography devices that are based on other principles, provided that a cylindrical planar x-ray detector can be utilized.

In the above embodiment, an example was presented in which, in FIG. 3A, the diffracted x-rays R1 irradiate the imaging plate 28 from the normal direction, or the direction at a right angle, but the diffracted x-rays R1 may also irradiate the imaging plate 28 from an oblique direction.

In the above embodiment, an example was presented in which a TDI/CCD unit 50 and a TV camera unit 51 were used as image formation means in addition to the imaging plate 28. However, cases in which only an imaging plate 28 is used, without a TDI/CCD unit 50 or TV camera unit 51, are also within the technological scope of the present invention.

In the above embodiment, the linear x-rays that scan the sample crystal 11 were curved x-rays, but simple linear x-rays may also be used.

What is claimed is:

1. An x-ray topography apparatus comprising:
    an x-ray source for generating x-rays;
    a first slit for forming the x-rays from the x-ray source into a linear shape and causing the x-rays to be incident on a sample;
    a scanning stage for moving the sample relative to the x-ray source;
    an x-ray detector for receiving the x-rays from the sample; and
    a second slit provided between the sample and the x-ray detector, wherein:
    a planar diffraction image is obtained by moving the sample by the scanning stage, keeping the second slit fixed in place relative to the x-ray source, and moving the x-ray detector in synchronization with the sample, while performing measurements of applying x-rays to the sample and receiving the x-rays from the sample by the x-ray detector;
    the x-ray detector is a planar x-ray detector of cylindrical shape having a surface area greater than the surface area of the sample;
    detector rotation means is provided for rotating the planar x-ray detector about a center axis of the cylindrical shape in coordination with a scanning movement of the linear x-rays;
    the center axis of the cylindrical shape extends in a direction at a right angle to the direction of the scanning movement of the linear x-ray; and
    the second slit is provided at an incline relative to the sample so that x-rays from the sample enter the x-ray detector from a normal line direction relative to the x-ray detector.

2. The x-ray topography apparatus according to claim 1, wherein the extension direction of the linear x-ray is a direction at a right angle to the direction of the scanning movement of the linear x-ray, and the center axis of the cylindrical shape of the planar x-ray detector extends parallel to the same direction as the extension direction of the linear x-ray.

3. The x-ray topography apparatus according to claim 2, wherein the detector rotation means rotates the planar x-ray detector so that a peripheral speed of an external peripheral surface of the planar x-ray detector and a scanning movement speed of the linear x-ray are the same.

4. The x-ray topography apparatus according to claim 2, wherein the planar x-ray detector has a cylindrical storage phosphor as a member irradiated with a diffracted x-ray from the sample, and
    the storage phosphor accumulates energy in a portion irradiated with the x-ray, and releases the energy as light emission when the portion is irradiated with light.

5. The x-ray topography apparatus according to claim 2, wherein the planar x-ray detector is disposed in a dark box,
    a read device and an erase device are provided around the planar x-ray detector in the dark box,
    the read device reads an image stored in the planar x-ray detector, and
    the erase device erases the image stored in the planar x-ray detector.

6. The x-ray topography apparatus according to claim 2, further comprising:
    a two-dimensional CCD sensor in which a plurality of CCD elements for receiving an x-ray and outputting a signal are arranged in a plane; and
    means for selectively placing either one of the planar x-ray detector and the two-dimensional CCD sensor at a position for detecting a diffracted x-ray from the sample.

7. The x-ray topography apparatus according to claim 6, further comprising:
    CCD control means for controlling an operation of the plurality of CCD elements and determining an x-ray intensity on the basis of an output signal from each of the CCD elements, wherein the CCD control means controls the plurality of CCD elements on the basis of a TDI method.

8. The x-ray topography apparatus according to claim 2, further comprising:
    a two-dimensional pixel detector in which a plurality of semiconductor x-ray detecting elements for receiving an x-ray and outputting a signal are arranged in a plane; and
    means for selectively placing either one of the planar x-ray detector and the two-dimensional pixel detector at a position for detecting a diffracted x-ray from the sample.

9. The x-ray topography apparatus according to claim 1, wherein the detector rotation means rotates the planar x-ray detector so that a peripheral speed of an external peripheral surface of the planar x-ray detector and a scanning movement speed of the linear x-ray are the same.

10. The x-ray topography apparatus according to claim 9, wherein the planar x-ray detector has a cylindrical storage phosphor as a member irradiated with a diffracted x-ray from the sample, and
    the storage phosphor accumulates energy in a portion irradiated with the x-ray, and releases the energy as light emission when the portion is irradiated with light.

11. The x-ray topography apparatus according to claim 9, wherein the planar x-ray detector is disposed in a dark box,
    a read device and an erase device are provided around the planar x-ray detector in the dark box,
    the read device reads an image stored in the planar x-ray detector, and the erase device erases the image stored in the planar x-ray detector.

12. The x-ray topography apparatus according to claim 9, further comprising:
- a two-dimensional CCD sensor in which a plurality of CCD elements for receiving an x-ray and outputting a signal are arranged in a plane; and
- means for selectively placing either one of the planar x-ray detector and the two-dimensional CCD sensor at a position for detecting a diffracted x-ray from the sample.

* * * * *